United States Patent [19]

Green et al.

[11] Patent Number: 5,217,472

[45] Date of Patent: Jun. 8, 1993

[54] SURGICAL FASTENING DEVICE

[75] Inventors: David T. Green, Westport; Henry Bolanos, East Norwalk; Dominick L. Mastri, Bridgeport; Richard A. McGarry, Norwalk, all of Conn.; Wayne P. Young, Brewster, N.Y.

[73] Assignee: United States Surgical Corporation, Norwalk, Conn.

[21] Appl. No.: 696,511

[22] Filed: May 7, 1991

[51] Int. Cl.$^5$ .............................................. A61B 17/00
[52] U.S. Cl. .................................... 606/139; 227/19; 227/175; 227/178; 227/182
[58] Field of Search ................. 606/139, 219; 227/19, 227/175, 176, 178, 179, 181; 411/457

[56] References Cited

U.S. PATENT DOCUMENTS

| 28,932 | 8/1876 | Noiles et al. ............................ 227/19 |
| 389,660 | 9/1888 | Mandel et al. . |
| 3,054,406 | 9/1962 | Usher ...................................... 606/151 |
| 3,124,136 | 3/1964 | Usher ...................................... 606/151 |
| 3,494,533 | 2/1970 | Green et al. ............................ 227/19 |
| 3,643,851 | 2/1972 | Green et al. ............................ 227/19 |
| 3,837,555 | 9/1974 | Green .................................... 227/130 |
| 4,014,492 | 3/1977 | Rothfuss .................................. 227/19 |
| 4,027,510 | 6/1977 | Hiltebrandt . |
| 4,043,504 | 8/1977 | Hueil et al. .............................. 227/19 |
| 4,127,227 | 11/1978 | Green ...................................... 227/83 |
| 4,196,836 | 4/1980 | Becht ...................................... 227/19 |
| 4,204,623 | 5/1980 | Green ...................................... 227/19 |
| 4,256,251 | 3/1981 | Moshofsky .............................. 227/19 |
| 4,261,244 | 4/1981 | Becht et al. .............................. 227/19 |
| 4,347,847 | 9/1982 | Usher .................................... 606/219 |
| 4,349,028 | 9/1982 | Green . |
| 4,375,866 | 3/1983 | Giersch et al. .......................... 227/19 |
| 4,403,693 | 9/1983 | Froehlich .............................. 411/472 |
| 4,407,286 | 10/1983 | Noiles . |
| 4,452,245 | 6/1984 | Usher . |
| 4,489,875 | 12/1984 | Crawford et al. ...................... 227/19 |
| 4,496,090 | 1/1985 | Crevier et al. .......................... 227/19 |
| 4,505,273 | 3/1985 | Braun et al. . |
| 4,509,518 | 4/1985 | McGarry et al. ...................... 606/143 |
| 4,520,817 | 6/1985 | Green . |
| 4,523,695 | 6/1985 | Braun et al. ............................ 227/19 |
| 4,523,707 | 6/1985 | Blake, III et al. ...................... 227/19 |
| 4,526,174 | 7/1985 | Froehlich .............................. 227/19 |
| 4,532,927 | 8/1985 | Miksza, Jr. ............................ 606/219 |
| 4,566,620 | 1/1986 | Green et al. ............................ 227/19 |
| 4,583,670 | 4/1986 | Alvarado .............................. 227/19 |
| 4,607,638 | 8/1986 | Crainich .............................. 411/472 |
| 4,610,251 | 9/1986 | Kumar . |
| 4,616,650 | 10/1986 | Green et al. .......................... 606/134 |
| 4,618,086 | 10/1986 | Li et al. .................................. 227/19 |
| 4,624,254 | 11/1986 | McGarry et al. ...................... 606/143 |
| 4,634,035 | 1/1987 | Li et al. .................................. 227/19 |

(List continued on next page.)

FOREIGN PATENT DOCUMENTS 2330182 1/1975 Fed. Rep. of Germany .
2703529 8/1978 Fed. Rep. of Germany .

OTHER PUBLICATIONS

Publication Entitled "A Quick Stapler Tie-Over Fixation For Skin Grafts", by Haim Y. Kaplan, M.D., Ann. Plast. Surg., 22:173, 1989, pp. 173-174.

Publication Entitled "A Rapid and Effective Method of Skin Graft Stabilization In Burned Children", by J. B. Boyd et al., The Hospital For Sick Children, Toronto, Canada, 1982, pp. 400-401.

Publication Entitled "A Simple Bolster Technique For Skin Grafting", by Henry T. Hoffman, M.D. and Michael LaRouere, M.D., Department of Otolaryngology, University of Michigan, Laryngoscope 99, May 1989, p. 558.

(List continued on next page.)

Primary Examiner—Stephen C. Pellegrino
Assistant Examiner—Gary Jackson
Attorney, Agent, or Firm—Thomas R. Bremer; Peter G. Dilworth; Rocco S. Barrese

[57] ABSTRACT

A surgical instrument for placing fasteners and/or a reinforcement material in tissue is provided. The fasteners exit the fastener housing at at an angle to the longitudinal axis of the device to facilitate visualization and placement at the surgical site. A unique fastener may be formed in which the legs are in a substantially overlapping, longitudinally-spaced relation.

27 Claims, 4 Drawing Sheets

U.S. PATENT DOCUMENTS

| | | | |
|---|---|---|---|
| 4,655,221 | 4/1987 | Devereux . | |
| 4,662,555 | 5/1987 | Thornton | 227/19 |
| 4,664,305 | 5/1987 | Blake | 227/19 |
| 4,671,279 | 6/1987 | Hill | 227/19 |
| 4,719,917 | 1/1988 | Barrows et al. | 227/19 |
| 4,728,020 | 3/1988 | Green et al. | 227/19 |
| 4,747,531 | 5/1988 | Brinkerhoff et al. | 227/19 |
| 4,787,387 | 11/1988 | Burbank, III et al. | 411/457 |
| 4,802,478 | 2/1989 | Powell | 227/19 |
| 4,807,628 | 2/1989 | Peters et al. | 227/19 |
| 4,821,939 | 4/1989 | Green | 227/19 |
| 4,821,942 | 4/1989 | Richards et al. . | |
| 4,874,122 | 10/1989 | Froelich et al. | 606/219 |
| 4,899,745 | 2/1990 | Laboureau et al. | 606/142 |
| 4,919,152 | 4/1990 | Ger . | |
| 4,919,320 | 4/1990 | Storace | 227/19 |
| 4,934,364 | 6/1990 | Green | 606/143 |
| 4,944,443 | 7/1990 | Oddsen et al. | 227/19 |
| 4,978,049 | 12/1990 | Green . | |
| 5,125,553 | 6/1992 | Oddsen et al. . | |

OTHER PUBLICATIONS

U.S. patent application Ser. No. 07/631.373, filed Dec. 20, 1990, entitled "Fascia Clip".

U.S. patent application Ser. No. 07/686,795, filed Apr. 17, 1991, entitled "Fascia Clip and Instrument".

Information Booklet for Auto Suture © Multifire Premium TM Disposable Skin Stapler and Disposable Loading Unit.

Information Booklet for Auto Suture © Skin & Fascia Suture © Surgical Stapling Instruments.

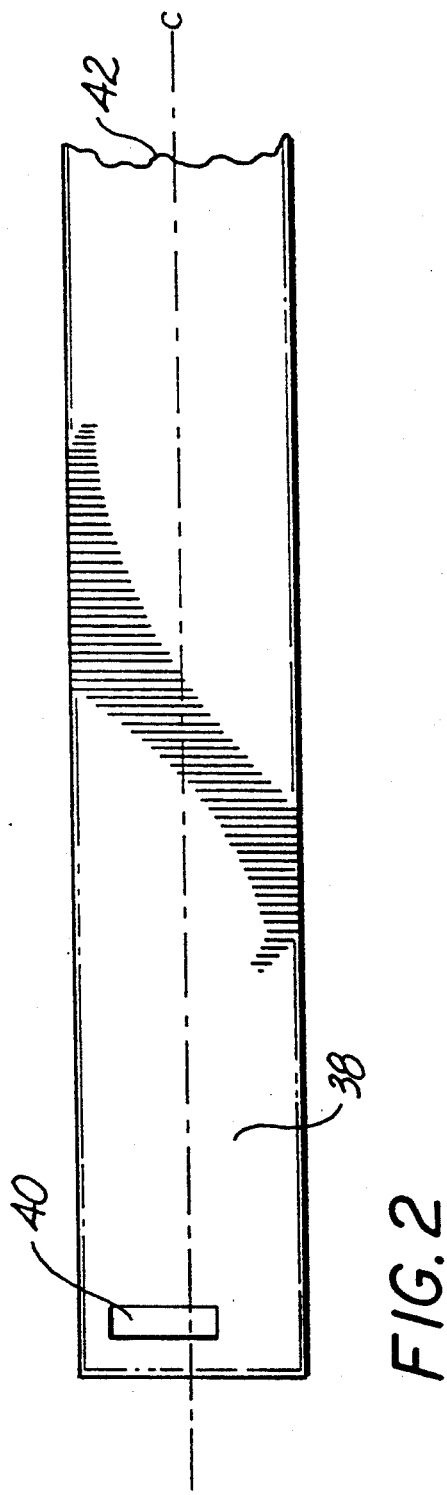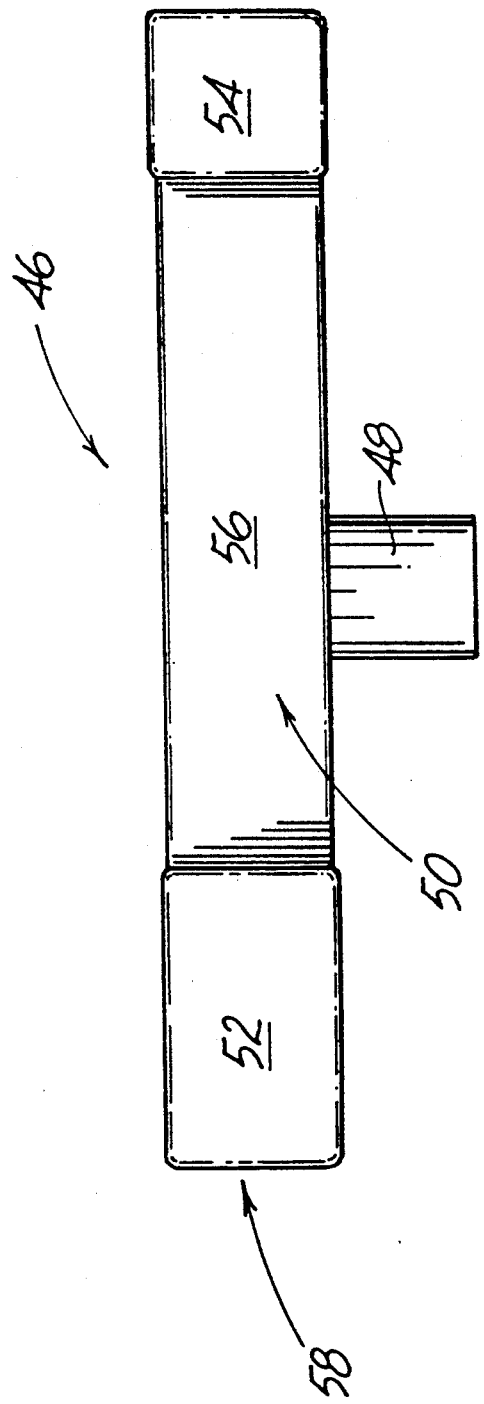

SURGICAL FASTENING DEVICE

TECHNICAL FIELD

The present invention relates to a device for applying clips or staples to tissue, and more particularly to a unique delivery system adapted for endoscopic application of clips/staples. The system is useful for repairing defects in the body wall, e.g., by securing a mesh to the wall in the region of the defect.

BACKGROUND OF THE INVENTION

The placement of clips and staples in surgical procedures is well known. For example, U.S. Pat. Nos. 4,616,650 to Green et al. and 4,934,364 to Green disclose clip appliers for placing clips, both absorbable and non-absorbable, on tissues and vessels. The clips are fed successively into the instrument jaws and cammed closed. Instruments for placing a plurality of staples on tissue and optionally cutting therebetween are disclosed in U.S. Pat. Nos. 3,494,533 to Green et al. and 4,520,817 to Green. The staples are supplied in pre-loaded cartridges and are formed through contact with oppositely positioned anvil pockets.

An important consideration in the design and utilization of surgical clip appliers and staplers is the visibility and ease of instrument positioning provided to the surgeon. One approach has been to provide a stapler having a fastener applying assembly that articulates relative to the actuator assembly, as disclosed in U.S. Pat. Nos. 4,566,620 and 4,728,020 to Green et al. It has also been suggested to provide a surgical clip applier with a longitudinally curved sleeve, as disclosed in U.S. Pat. Nos. 4,509,518 and 4,624,254 to McGarry et al., and 4,664,305 to Blake.

Instruments for surgically stapling disunited skin of a patient to effect joining of the skin are also known. These instruments typically form substantially box-shaped staples by bending each staple around an anvil placed against the skin, and may be adapted to permit rotation of the staple forming assembly relative to the handles. See, e.g., U.S. Pat. Nos. 3,643,851 to Green et al. and Re. 28,932 to Noiles et al. Fascia staplers have also been disclosed which form fascia staples having a unique geometry for holding fascia tissue. See, e.g., U.S. Pat. No. 4,127,227 to Green.

More recently, attention has focused on minimally-invasive surgical procedures and instruments for facilitating such procedures. Minimally-invasive procedures are typically performed endoscopically through trocar sleeves or cannulas. Prior to introducing the cannula through the body wall, the surgeon generally, insufflates the body cavity with carbon dioxide, e.g., through a Verres needle or like device. Insufflation creates a free area between internal body organs and the body wall. The surgeon then introduces one or more trocars through the body wall into the insufflated body cavity to create a port of entry for accessory instrumentation. For example, graspers, dissectors, clip appliers, lasers and electrocautery devices are routinely employed endoscopically with the visual assistance of an endoscope and an external television monitor.

Endoscopic cholecystectomy (gall bladder removal) has recently met with tremendous clinical success and acceptance. Another procedure receiving attention for adaptation as a minimally-invasive surgical technique is hernia repair, with attention being primarily directed to all types of inguinal hernias (direct, indirect and femoral). A hernia involves the protrusion of an inner organ or body part through a defect in the muscle wall by which it is ordinarily contained. Historically, hernia repair has been performed by pulling the muscles together around the defect and suturing the muscles together, closing the hole but creating tension on the sutures. More recently, hernia defects have been repaired by suturing mesh over the defect. This approach patches the defect rather than drawing the spaced muscle walls together and/or ligating the hernia sac.

In order to facilitate surgical procedures, and particularly endoscopic procedures such as hernia repair, instrumentation is needed which provides the surgeon with improved visibility and which facilitates positioning of the instrument at the surgical site. A fastening system to provide optimal securement of a mesh or like device, preferably endoscopically, is also needed. These and other objectives are achieved by the present invention.

SUMMARY OF THE INVENTION

In accordance with the present invention, a surgical instrument for placing fasteners in or on tissue is provided which includes:

(a) a fastener housing having anvil means mounted at one end thereof and adapted to house at least one fastener therein;

(b) pusher means slidably received by said fastener housing, the pusher means comprising a pusher bar which defines a longitudinal axis and a pusher element slidably mounted to the pusher bar; and (c) slot means in the fastener housing, wherein the pusher means cooperates with the slot means to angularly displace the pusher element with respect to the longitudinal axis as the pusher means is advanced through the fastener housing.

The surgical instrument of the invention is thus adapted to angularly deliver a fastener to tissue with respect to the longitudinal axis of the instrument. Such angular delivery provides improved visibility to the surgeon and facilitates fastener placement in difficult tissue locations. The instrument is particularly suited for endoscopic applications, e.g., for securing a mesh to tissue in hernia repair.

In a preferred embodiment, the fastener housing contains a plurality of fasteners for sequential placement in tissue. Means are provided for advancing the fasteners distally and further means are provided for preventing more than one fastener from being placed in the "ready" position. A fastener may be placed by actuating handle means, e.g., a pistol handle, which effects distal movement of the pusher means. The fastener housing is preferably rotatable with respect to the handle means to further facilitate visibility and fastener placement.

According to the present invention, fasteners are angularly delivered to tissue through cooperation between slot means, pin means and cam means. The pusher element includes a contact face which is adapted to advance a fastener into engagement with and formation against the anvil means. The pusher element travels within a fastener track in the fastener housing, the width of which is only slightly larger than the width of the pusher element contact face. The pusher element is slidably mounted to the pusher bar by pin means extending through a transverse slot formed at the distal end of the pusher bar. Further slot means are formed in the fastener housing below the pusher bar. The pin means extends through the transverse slot to ride within the fastener housing slot means.

The fastener housing slot means causes the pusher element to jog as follows:

(i) the fastener housing slot means includes a first slot region which extends along the longitudinal axis of the instrument; the contact face of the pusher element is substantially perpendicular to the longitudinal axis of the instrument as the pin means travels within the first slot region;

(ii) distal to the first slot region, a second slot region communicates with and is angularly oriented with respect to the first slot region; inasmuch as the pusher element is constrained in its transverse movement by the fastener track, as the pin means enters the second slot region the pin means moves within the transverse slot formed in the pusher bar and the pusher element rotates with respect to the pusher bar; and (iv) a third slot region communicates with the second and extends at an angle to the longitudinal axis of the instrument opposite to that of the second slot region; as the pin means enters the third slot region the pusher element is prevented from returning to its initial non-rotated orientation through contact with a cam face extending into the fastener track; thus, as the pin means moves back within the transverse slot, the pusher element retains its rotated position with respect to the pusher bar.

A unique fastener-forming assembly is also provided according to the present invention which includes:

(a) a fastener housing defining a fastener track having a center line and an opening at one end adapted to permit fastener exit;

(b) anvil means positioned adjacent the exit opening, the anvil means being positioned in a transverse and non-symmetrical orientation with respect to the center line; and (c) a fastener having a backspan and a pair of legs extending from the backspan at either end thereof; wherein contact of the fastener with the non-symmetrically positioned anvil causes the backspan of the fastener to bend such that the fastener legs assume a substantially over-lapping, longitudinally-spaced relation.

The fastener-forming assembly of the invention facilitates formation of a fastener particularly suited for securing an article, e.g., a reinforcement mesh, to tissue, as for example in hernia repair. The over-lapping configuration of the formed fastener allows the fastener legs to advance further than prior art fasteners prior to bending, thus facilitating fastener placement. Moreover, the substantially over-lapping, longitudinally-spaced orientation of the fastener legs provides excellent holding power when embedded in tissue. Preferably, the means for advancing the fastener into contact with the anvil means comprises a U-shaped pusher element having legs of differing widths so as to cooperate with the non-symmetrically positioned anvil means.

The instruments of the present invention are specially suited for endoscopic applications. In such cases, the fastener formation system is typically fabricated as part of an endoscopic portion which is adapted for introduction through a trocar sleeve having a diameter of, for example, 10 to 15 mms. Internal sealing means are typically provided in the instrument, e.g., a sealing block, to ensure a gaseous seal when working in an insufflated body cavity.

BRIEF DESCRIPTION OF THE DRAWINGS

The accompanying figures referred to herein and constituting a part hereof illustrate preferred embodiments of the present invention, and together with the description, serve to explain the principles of the invention.

FIG. 2 is a top view of a portion of a pusher bar;

FIG. 3 is a front view of a pusher element of the invention;

DETAILED DESCRIPTION OF THE INVENTION

A variety of actuation and fastener feeding mechanisms may be employed to advance the pusher means of the surgical instrument of the present invention to form and place fasteners. For example, the principles of the present invention may be adapted for use with a variety of handle configurations, e.g., pistol grips, scissor grips, palm grip, etc. Similarly, the fasteners of the invention may be stored and individually placed in the "ready" position using a variety of known mechanisms. Illustrative of such mechanisms are the pinion gear/pinion shaft mechanism and related structure disclosed in U.S. Pat. No. Re. 28,932 to Noiles et al., the belt mechanism and related structure disclosed in U.S. Pat. No. 3,837,555 to Green, and the mechanism and related structure of U.S. Pat. No. 4,204,623 to Green. The contents of these three commonly assigned U.S. patents are hereby incorporated by reference.

The present invention may be fabricated as a single, unitary assembly intended for single or multiple use, or practiced in association with a reusable actuating assembly which is adapted to receive a plurality of pre-loaded cartridges, whether in a single surgical procedure or, after sterilization, in further procedures. Such choices are well within the skill of one of ordinary skill of the art and are deemed to be within the scope of the present invention.

The remaining description shall be directed to fastener advancement and formation from the point at which a single fastener has been placed in the "ready" position, i.e., positioned adjacent pusher means adapted to advance the fastener into contact with the anvil means. As noted above, a variety of mechanisms and structure may be employed to position a fastener in the ready position.

Figure 1:
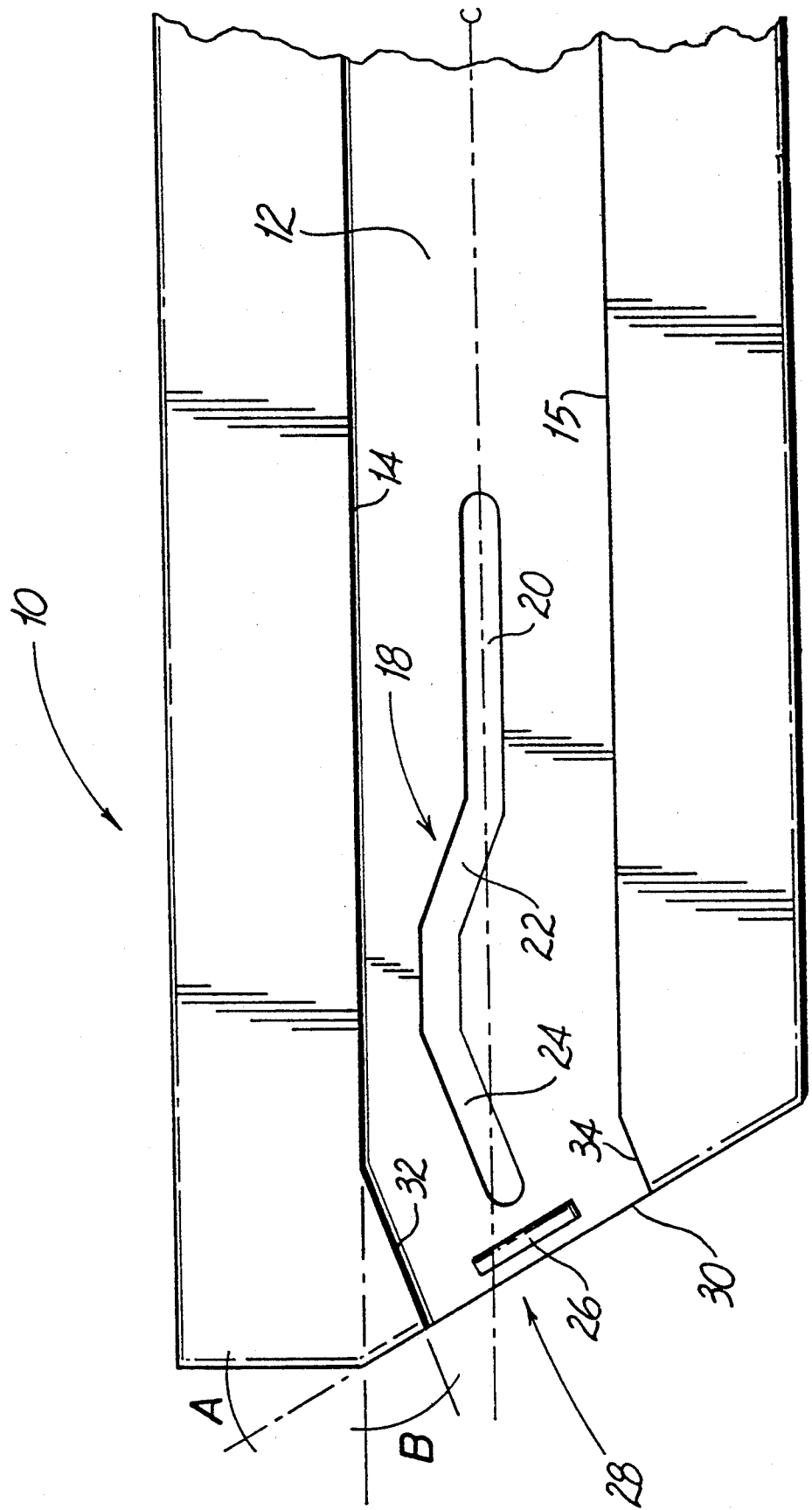
FIG. 1 is a schematic plan view of a distal portion of a fastener housing according to the present invention.

With reference FIG. 1, a schematic plan view of the fastener housing in the region of fastener delivery is provided. Fastener housing 10 includes a fastener track 12 which extends substantially along the longitudinal axis of fastener housing 10. Fastener track 12 is defined by track walls 14, 15. Fastener track 12 is sized and dimensioned to receive an unformed fastener 44, as discussed hereinbelow.

A slot 18 is formed in fastener track 12 toward the distal end of fastener housing 10. Slot 18 comprises first slot region 20, second slot region 22 and third slot region 24. First slot region 20 extends substantially along the longitudinal axis of fastener housing 10. Second slot region 22 communicates with and is angularly oriented with respect to first slot region 20. Third slot region 24 communicates with and is angularly oriented with respect to second slot region 22. More particularly, third slot region 24 extends at an angle to the longitudinal axis of fastener housing 10 which is opposite to the angle of second slot region 22. Although, as illustrated, first and second slot regions 22, 24 are linear, a variety of geometrics are possible, as for example arcuate slot paths.

An anvil 26 is positioned adjacent the outlet of fastener track 12. Anvil 26 is spaced from the termination of slot 18. Anvil 26 comprises a rigid material, e.g., stainless steel, which is sized and dimensioned to facilitate fastener formation therearound. Although FIG. 1 shows a single anvil 26 positioned in fastener track 12, additional anvil means are contemplated for incorporation into the instrument of the present invention, as for example the dual anvil sections (106,108) of U.S. Pat. No. 4,127,227 to Green, previously incorporated by reference.

The distal end 28 of fastener housing 10 includes an angled face 30 which is at an Angle A to the transverse axis of fastener housing 10. Angle A of angled face 30 is generally about 5° to 45° and preferably 15° to 25° relative to the transverse axis of fastener housing 10. Angle A may be greater than 45° or less than 5° by making appropriate adjustments to slot 18 and fastener track walls 14, 15, as discussed below.

Fastener track wall 14 forms an inwardly directed cam face 32 at its distal end. A corresponding, outwardly directed wall section 34 is formed at the distal end of track wall 15. By "inwardly" and "outwardly" directed is meant toward and away from the center line of fastener track 12, respectively. Cam face 32 and wall section 34 are preferably at an Angle B to the longitudinal axis of fastener housing 10. Angles A and B are preferably substantially equal.

Inwardly directed cam face 32 and outwardly directed wall section 34 cause fastener track 12 to angle with respect to the longitudinal axis of fastener housing 10. The width of fastener track 12 remains substantially constant throughout, i.e., in both its longitudinally oriented and angled regions. Third slot region 24 is typically at the same angle to the longitudinal axis as cam face 32 and wall section 34, i.e., Angle B. Anvil 26 is positioned transverse to the angled region of fastener track 12.

Referring to FIG. 2 and an elongated pusher bar 38 is slidably received within fastener track 12. Pusher bar 38 includes a transverse slot 40 at its distal end. Transverse slot 40 is assymetric with respect to the center line of pusher bar 38. The proximal end 42 of pusher bar 38 is adapted to cooperate with an actuating mechanism which effectuates longitudinal movement of pusher bar 38 within fastener track 12 to advance and form a fastener 44.

Figure 4:
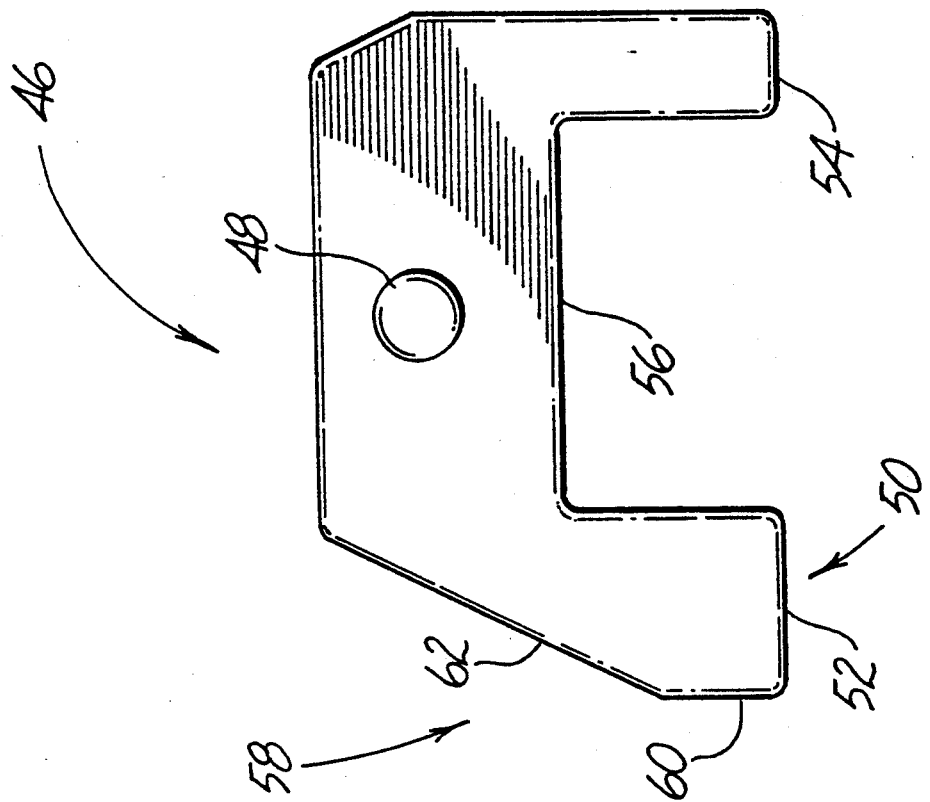
FIG. 4 is a bottom view of the pusher element.

As shown in FIGS. 3 and 4, a U-shaped pusher element 46 includes a downwardly extending pin 48. Pusher element 46 also includes a contact face 50 which includes distally directed pusher legs 52, 54 and a substantially U-shaped region 56. Side wall 58 includes a longitudinally directed side face 60 and an angled abutment face 62. Pin 48 is sized and dimensioned to extend through and ride with transverse slot 40 in pusher bar 38, and to further extend into and ride within slot 18 in fastener track 12.

Figure 6:
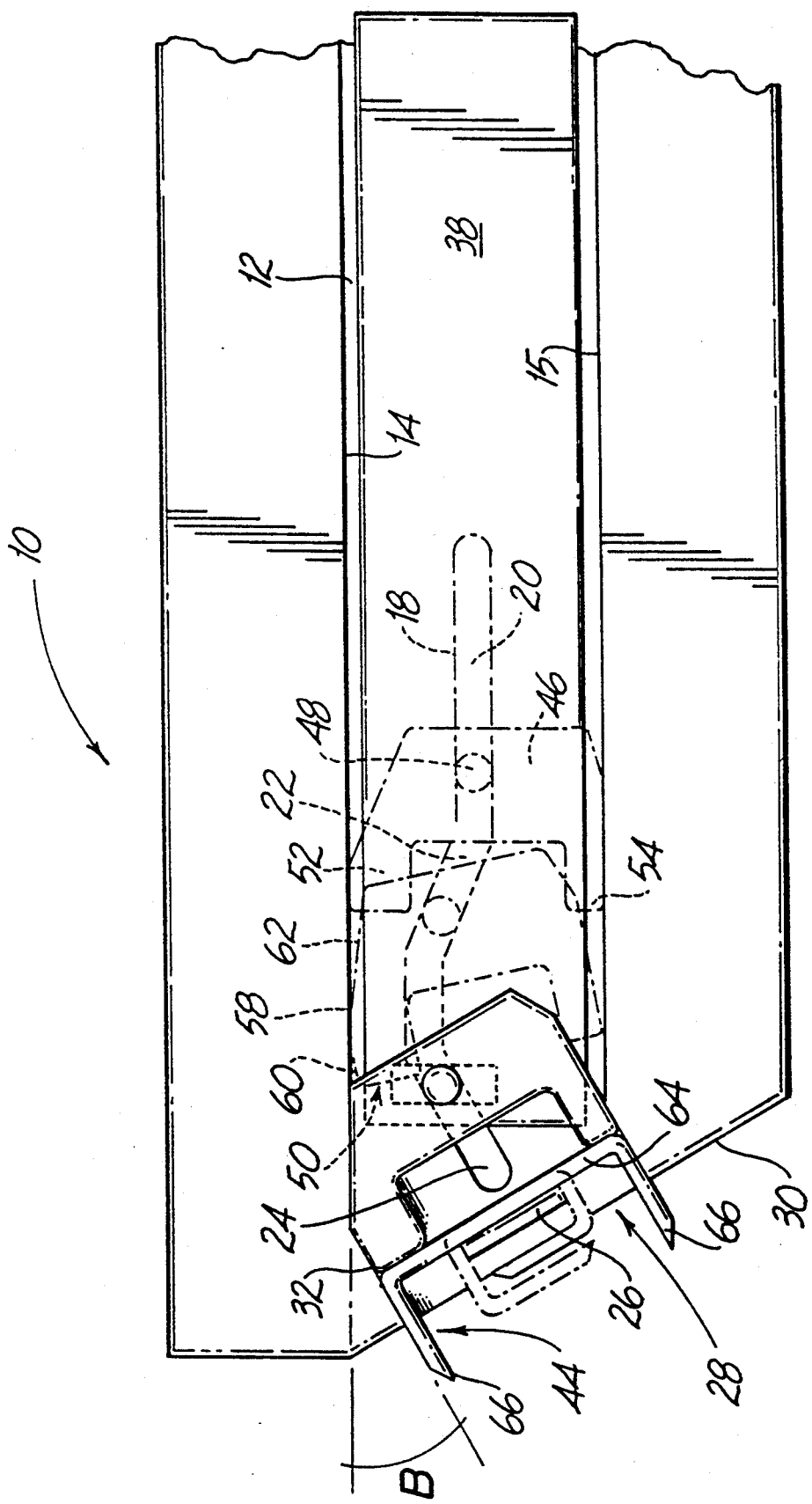
FIG. 6 is a schematic plan view of a distal portion of the fastener housing of FIG. 1 at various stages of fastener advancement.

Referring to FIG. 6, the interaction and cooperation of pusher bar 38, pusher element 46, fastener track 12, slot 18 and anvil 26 will now be described. FIG. 6 shows the above elements at various stages of fastener advance. Fastener 44 is positioned distal of and in abutment with contact face 50 of pusher element 46. In the proximal-most pictured position of pusher element 46, pin 48 is located within first slot region 20 and within transverse slot 40 to substantially at the center line of pusher bar 38.

As the pusher bar 38 is advanced distally, pin 48 enters second slot region 22 which causes pin 48 to travel within transverse slot 40 toward track wall 14. Contact between side face 60 of pusher element 46 and track wall 14 prevents transverse displacement of pusher element 46 with respect to fastener track 12 and causes counterclockwise rotation of pusher element 46 around pin 48. This counterclockwise rotation brings angled abutment face 62 into contact with track wall 14 (pusher element 46 is illustrated just prior to complete rotation). Contact face 50 of pusher element 46 thus assumes an angled orientation with respect to the longitudinal axis of fastener housing 10. Fastener 44 is brought into the same angled orientation through interaction with contact face 50. Contact face 50 and fastener 44 are preferably oriented at an Angle B to the longitudinal axis of fastener housing 12.

Figure 5:
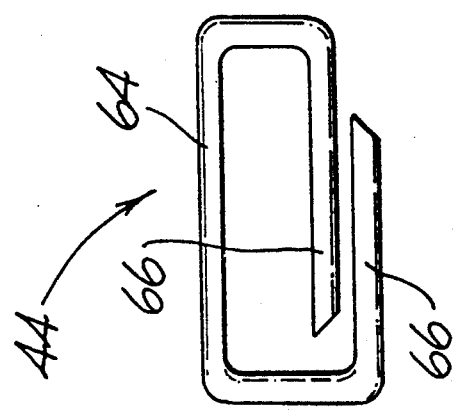
FIG. 5 is a schematic view of a preferred, formed fastener.

Further distal movement of pusher bar 38 causes pin 48 to enter third slot region 24. As pin 48 reaches third slot region 24, side wall 58 of pusher element 46 comes into contact with inwardly directed cam face 32. Pin 48 travels within transverse slot 40 toward track wall 15 as it moves distally within third slot region 24. Fastener 44 is thus advanced through the angled portion of fastener track 12. Backspan 64 of fastener 44 engages anvil 26 and pusher legs 52, 54 drive fastener 44 so as to bend fasteners legs 66 therearound (see also FIG. 5). Fastener 44 is fully formed at such time as pin 48 reaches the distal termination of slot 18.

In use, the surgeon places angled face 30 of fastener housing 10 adjacent to or against the tissue, reinforcement material or the like, to be fastened. The surgeon may, if he wishes, advance pusher bar 38 and thus fastener 44 to expose fastener legs 66 from fastener housing 10 prior to so placing fastener housing 10, to facilitate proper placement of fastener 44. Thereafter, pusher bar 38 is advanced to form fastener 44 in or around the tissue and/or reinforcement material, e.g., mesh, to be fastened.

In a preferred embodiment of the invention, fastener 44 is formed in a unique configuration which provides significant clinical advantages, particularly when used to fasten a reinforcement material to tissue, e.g., in hernia repair. The unique fastener configuration is accomplished by (i) positioning anvil 26 assymetrically with respect to the center line of the angled portion of fastener track 12 and (ii) providing a pusher member 42 adapted to cooperate with assymetrically positioned anvil 26 and preferably including contact legs 52, 54 of differing widths. In forming this unique fastener 44, the surgeon is able to expose greater lengths of fastener legs 66 to facilitate visualization and optimal placement because, when formed, legs 66 assume a substantially overlapping, longitudinally-spaced relation.

Referring to FIGS. 3, 4 and 6, contact leg 52 of pusher member 42 has a greater width than contact leg 54. Anvil 26 is positioned assymetrically with respect to the center line of the angled portion of fastener track 12, being positioned more toward the side on which thinner contact leg 54 travels.

As pusher member 42 approaches anvil 26, contact legs 52, 54 pass on either side thereof. Fastener 44 is thus bent into the configuration shown in FIG. 5, with legs 66 in substantially overlapping, longitudinally-spaced relation. The arcuate travel of legs 66 as they are bent into their final configuration provides an advantageous bite into tissue and/or reinforcement material, and the overlapping, longitudinally-spaced relation provides excellent holding power. Preferably fastener legs 66, when formed, are in a substantially parallel orientation, although the exact degree to which fastener legs 66 are parallel will generally depend on the resilience of the substrate into which they are fastened.

While the above description contains many specifics, these specifics should not be construed as limitations on the scope of the invention, but nearly as exemplifications of preferred embodiments thereof. Those skilled in the art will envision many other possible variations that are within the scope and spirit of the invention as defined by the claims appended hereto.

We claim:

1. A surgical instrument for placing a fastener in or on tissue comprising:
   (a) a fastener housing having anvil means mounted at one end thereof and adapted to house at least one fastener therein;
   (b) pusher means slidably received by said fastener housing, said pusher means comprising a pusher bar which defines a longitudinal axis and a pusher element slidably mounted to said pusher bar; and
   (c) slot means in said fastener housing, wherein said pusher means cooperates with said slot means to angularly displace said pusher element with respect to said longitudinal axis as said pusher means is advanced through said fastener housing.

2. The surgical instrument of claim 1, wherein said fastener housing includes a fastener track, said fastener track being sized and dimensioned to receive said at least one fastener.

3. The surgical instrument of claim 2, wherein said anvil means is mounted assymetrically with respect to a center line of said fastener track.

4. The surgical instrument of claim 1, wherein said anvil means comprises an anvil.

5. The surgical instrument of claim 1, wherein said anvil means comprises dual anvil components.

6. The surgical instrument of claim 1, wherein said fastener housing comprises an endoscopic portion.

7. The surgical instrument of claim 1, wherein said pusher bar has a transverse slot toward a distal end thereof.

8. The surgical instrument of claim 7, wherein said pusher element includes pin means adapted to travel within said transverse slot.

9. The surgical instrument of claim 8, wherein said pin means is further adapted to travel within said slot means.

10. The surgical instrument of claim 1, wherein said pusher element is angularly displaced by about 5 to about 45 degrees with respect to said longitudinal axis.

11. The surgical instrument of claim 1, wherein said pusher element is angularly displaced by about 15 to about 25 degrees with respect to said longitudinal axis.

12. The surgical instrument of claim 1, wherein said fastener housing is structured and dimensioned to house at least one fastener adapted to secure a reinforcement material in or on tissue.

13. The surgical instrument of claim 12, wherein said fastener housing is structured and dimensioned to house at least one fastener adapted to secure reinforcement mesh material to tissue in endoscopic hernia repair.

14. A fastener-forming assembly comprising:
   (a) a fastener housing defining a fastener track having a center line and an opening at one end adapted to permit fastener exit;
   (b) anvil means positioned adjacent said opening, said anvil means being positioned in a transverse and non-symmetrical orientation with respect to said center line; and
   (c) a fastener having a backspan and a pair of legs extending from the backspan at either end thereof; wherein contact of said fastener with said non-symmetrically positioned anvil causes said backspan of said fastener to bend such that said fastener legs assume a substantially over-lapping, longitudinally-spaced relation.

15. The surgical instrument of claim 14, wherein said fastener-forming assembly further comprises a substantially U-shaped pusher element slidably received in said fastener housing.

16. The surgical instrument of claim 15, wherein said U-shaped pusher element includes first and second distally directed legs and wherein said first leg is wider than said second leg.

17. The surgical instrument of claim 16, wherein said fastener legs assume a substantially parallel relation.

18. The surgical instrument of claim 14, wherein said fastener is adapted to secure a reinforcement material to tissue.

19. The surgical fastener of claim 2, wherein at least portions of said legs closest to said backspan are substantially parallel to each other.

20. In combination with a fastener forming assembly having a fastener housing defining a fastener track having a center line and an opening at one end adapted to permit fastener exit, a surgical fastener having:

a backspan having a pair of legs extending from said backspan at either end thereof and generally perpendicular thereto, and anvil means asymmetrically positioned with respect to said center line of said housing whereby each leg may be bent inwardly toward the other, each leg being of length sufficient to form a pair of inwardly extending leg portions which overlap each other at least over substantial portions of their entire length and positioned in adjacent unconnected relation, the distance between said overlapping leg portions and said backspan being sufficient to receive an object such as surgical mesh therebetween to attach the object to body tissue whereby said backspan and said legs form a substantially rectangular configuration.

21. In combination with a fastener forming assembly having a fastener housing defining a fastener track having a center line and an opening at one end adapted to permit fastener exit, a surgical fastener for attaching an object such as surgical mesh to body tissue in endoscopic hernia surgery, said fastener having a backspan having a pair of legs extending from said backspan at either end and generally perpendicular thereto, and an anvil asymmetrically positioned with respect to said housing whereby each leg may be bent inwardly toward the other to form a closed configuration, each leg being of length sufficient such that the distance between said inwardly bent leg portions and said backspan is sufficient to receive an object such as surgical mesh therebetween to attach the object to body tissue whereby said backspan and said legs form a substantially rectangular configuration.

22. The surgical fastener of claim 21 wherein each said leg is of sufficient length such that said inwardly bent portions are in substantially overlapping relation.

23. The surgical fastener of claim 22 wherein said inwardly extending leg portions overlap each other at least over substantial portions of their entire length.

24. A method of forming a surgical fastener comprising:
 (a) providing a fastener having a backspan and a pair of legs extending generally perpendicular to said backspan and in generally parallel relation to each other;
 (b) providing anvil means asymmetrically positioned between said legs at a location for contact by said backspan;
 (c) advancing said fastener against said anvil means to form said fastener whereby at least a portion of each of said legs assumes a substantially parallel relation with at least a portion of said other leg and said fastener assumes a substantially rectangular configuration adapted to attach an object such as surgical mesh to body tissue.

25. Apparatus according to claim 24 wherein said legs are of sufficient length to move inwardly about said anvil means so as to receive the body tissue and attached object between said backspan and said inwardly extending legs.

26. A system for applying staples in endoscopic hernia surgery to attach an object such as surgical mesh to body tissue which comprises:
 (a) a plurality of staples, each having a backspan and a pair of legs extending generally perpendicular from said backspan;
 (b) anvil means asymmetrically positioned with respect to said staples for forming each staple; and
 (c) pusher means adapted to advance each said staple into contact with said anvil means, said pusher means and said anvil means being configured, dimensioned and relatively positioned and adapted to contact each staple asymmetrically to thereby cause said legs to move inwardly toward each other in a manner to form a generally rectangular configuration, said legs further being of dimension sufficient to attach the object to the body tissue.

27. Apparatus for endoscopic application of staples to attach an object such as surgical mesh to body tissue, which comprises:
 a) endoscopic means for supporting a plurality of staples configured and adapted for attachment of the object to body tissue, each said staple including a backspan having a pair of legs extending therefrom, each leg having a sharp tip portion for penetrating the object and body tissue;
 b) anvil means positioned at the distal end of said endoscopic means and asymmetrically with respect to said legs for asymmetrically forming each staple; and
 c) means for advancing said staples into contact with said anvil means for individually forming said staples into a substantially rectangular configuration, each leg being of length sufficient to attach the object to the body tissue.

* * * * *